US012102086B2

(12) United States Patent
Wang et al.

(10) Patent No.: US 12,102,086 B2
(45) Date of Patent: Oct. 1, 2024

(54) **ANTIMICROBIAL PEPTIDE Spampcin$_{56-86}$ FROM *SCYLLA PARAMAMOSAIN* AND APPLICATIONS THEREOF**

(71) Applicant: XIAMEN UNIVERSITY, Xiamen (CN)

(72) Inventors: Kejian Wang, Xiamen (CN); Manyu Jiang, Xiamen (CN); Fangyi Chen, Xiamen (CN)

(73) Assignee: XIAMEN UNIVERSITY, Fujian (CN)

( * ) Notice: Subject to any disclaimer, the term of this patent is extended or adjusted under 35 U.S.C. 154(b) by 0 days.

(21) Appl. No.: 18/454,855

(22) Filed: Aug. 24, 2023

(65) Prior Publication Data

US 2023/0404076 A1    Dec. 21, 2023

Related U.S. Application Data

(63) Continuation-in-part of application No. PCT/CN2022/100406, filed on Jun. 22, 2022.

(30) Foreign Application Priority Data

Jun. 25, 2021 (CN) .......................... 202110716770.6

(51) Int. Cl.
| | | |
|---|---|---|
| *A61K 38/17* | (2006.01) | |
| *A01N 37/46* | (2006.01) | |
| *A01P 1/00* | (2006.01) | |
| *A01P 3/00* | (2006.01) | |
| *A23K 20/195* | (2016.01) | |
| *A23K 50/80* | (2016.01) | |
| *C07K 14/435* | (2006.01) | |

(52) U.S. Cl.
CPC ............... *A01N 37/46* (2013.01); *A01P 1/00* (2021.08); *A01P 3/00* (2021.08); *A23K 20/195* (2016.05); *A23K 50/80* (2016.05); *A61K 38/1767* (2013.01); *C07K 14/43509* (2013.01)

(58) Field of Classification Search
CPC .................. A23K 20/195; A23K 50/80; A61K 38/1767; C07K 14/43509
See application file for complete search history.

(56) References Cited

U.S. PATENT DOCUMENTS

| 3,786,142 A | 1/1974 | Motoo Shibata et al. |
| 10,208,088 B1 | 2/2019 | Du et al. |
| 2015/0104492 A1 | 4/2015 | McDermott et al. |

FOREIGN PATENT DOCUMENTS

| CN | 102167736 A | 8/2011 |
| CN | 103789317 A | 5/2014 |
| CN | 105274134 A | 1/2016 |
| CN | 110028568 A | 7/2019 |
| CN | 111051335 A | 4/2020 |
| CN | 112159460 A | 1/2021 |
| CN | 112724221 A | 4/2021 |
| CN | 112955460 A | 6/2021 |
| CN | 113307855 A | 8/2021 |
| KR | 102146779 B1 | 8/2020 |
| NL | 6614348 A | 4/1967 |
| WO | 0018798 A1 | 4/2000 |

OTHER PUBLICATIONS

Translation of parent application PCT/CN2022/100406 (Jun. 22, 2022). (Year: 2022).*
Translation of CN113307855A (Aug. 27, 2021). (Year: 2021).*
Corresponding International Patent Application No. PCT/CN2022/100406, International Search Report, date mailed Sep. 21, 2022.
Corresponding International Patent Application No. PCT/CN2022/100406, Written Opinion of the Searching Authority, date mailed Sep. 21, 2022.
Wang, Kejian, et al., "Progress in the Discovery, Study and Application of New Antimicrobial Peptides from Scylla Paramamosain", Journal of Xiamen University (National Science), Mar. 28, 2021, vol. 60, No. 2, pp. 408-412, with English abstract.
Hu, Fengxiao, et al., "Research Advances on Antimicrobial Peptides in Aquatic Animals", Fisheries Science, Nov. 27, 2019, vol. 38, No. 6, pp. 875-877, with English abstract.
Imjongjirak, C., et al., "Characterization and antimicrobial evaluation of SpPR-AMP1, a proline-rich antimicrobial peptide from the mud crab *Scylla paramamosain*", Developmental and Comparative Immunology, May 4, 2017, vol. 74, No. 4.

* cited by examiner

*Primary Examiner* — Jeffrey E. Russel
(74) *Attorney, Agent, or Firm* — Cooper Legal Group, LLC

(57) ABSTRACT

An antimicrobial peptide Spampcin$_{56-86}$ from *Scylla paramamosain* is provided. A molecular formula of the antimicrobial peptide Spampcin$_{56-86}$ is $C_{154}H_{256}N_{54}O_{33}S_3$, and an amino acid sequence of the antimicrobial peptide Spampcin$_{56-86}$ is shown in SEQ ID NO: 01.

6 Claims, 9 Drawing Sheets

Specification includes a Sequence Listing.

SEQUENCE LISTING

```
Sequence total quantity: 1
SEQ ID NO: 1           moltype = AA  length = 31
FEATURE                Location/Qualifiers
source                 1..31
                       mol_type = protein
                       organism = Scylla Paramamosain
SEQUENCE: 1
RRAAHGLLPR LRAPPPFHKR CVCLCRTAPP P                              31
```

ANTIMICROBIAL PEPTIDE Spampcin$_{56-86}$ FROM *SCYLLA PARAMAMOSAIN* AND APPLICATIONS THEREOF

RELATED APPLICATIONS

This application is a continuation-in-part of International patent application PCT/CN2022/100406, filed on Jun. 22, 2022, which claims priority to Chinese patent application 202110716770.6, filed on Jun. 25, 2021. International patent application PCT/CN2022/100406 and Chinese patent application 202110716770.6 are incorporated herein by reference.

REFERENCE TO AN ELECTRONIC SEQUENCE LISTING

The contents of the electronic sequence listing (Sequence-Listing.xml; Size: 1,958 bytes; and Date of Creation: Dec. 15, 2023) is herein incorporated by reference.

FIELD OF THE DISCLOSURE

The present disclosure relates to the field of marine molecular biotechnology, and in particular relates to an antimicrobial peptide Spampcin$_{56-86}$ from *Scylla paramamosain* and applications thereof.

BACKGROUND OF THE DISCLOSURE

It is reported that China is currently the largest producer and consumer of antibiotics in the world and is also one of the countries with the most serious drug resistant bacteria. The large amount of unregulated and irrational use of antibiotics has caused a series of problems, such as increased bacterial resistance, suppressed animal immunity, affected human health, and even damaged ecological environment. Therefore, the development of new and efficient anti-bacterial drugs and the search for effective antibiotic alternatives have become an urgent problem to be solved.

Antimicrobial peptides (AMPs) are a kind of small-molecule anti-microbial peptides and are widely distributed in animals and plants. AMPs are the first line of defense against infections of various pathogenic microorganisms and are an important part of the innate immune system. A main disease resistance mechanism of AMPs is to act on cell membranes of pathogenic microorganisms to enable the pathogenic microorganisms to have difficulty in producing resistance, so that a generation of drug resistance problems is avoided. AMPs have a broad spectrum of anti-bacterial activity, anti-fungal activity, anti-viral activity, anti-parasitic activity, and other activities. In addition, AMPs have multiple roles, such as acting as immunomodulators, signaling molecules, and anti-tumor molecules, etc. Therefore, AMPs are very attractive alternatives to traditional antibiotics and important candidates for the development of new antimicrobial drugs, and AMPs also have considerable prospects in transformation applications.

The structure of AMPs mainly consists of α-helix, β-sheet, and extended cyclic structures. Based on a number of charges carried, AMPs are classified into cationic and anionic peptides. Until now, the antimicrobial peptides database (CAMPR3) has collected 10247 natural and synthetic peptides. AMPs with a broad antimicrobial spectrum have also been found in marine animals, such as Crustins, ALFs, Penaeidins in shrimp hemolymph, Sphistin from histone H2A, glycine-rich new antimicrobial peptide (AMP) Spgly-AMP, and scygonadin and SCY2 derived from *Scylla serrata* with reproductive immune functions. The marine animals are living in extreme marine environments and lack acquired immunity. When pathogen infection occurs, AMPs and immune effective factors in the innate immunity fight against the pathogens. In recent years, with the continuous deterioration of the marine ecological environment, the problem of frequent occurrence of mariculture diseases has become increasingly prominent. Therefore, it is still of great significance to accelerate the research and development of novel AMPs.

BRIEF SUMMARY OF THE DISCLOSURE

A first object of the present disclosure is to provide a novel, safe, and efficient antimicrobial peptide (AMP) Spampcin$_{56-86}$ from *Scylla paramamosain* (i.e., Spampcin$_{56-86}$) and applications thereof.

A second object of the present disclosure is to provide applications for using the Spampcin$_{56-86}$.

A first technical solution is as follows.

The molecular formula of the Spampcin$_{56-86}$ is $C_{154}H_{256}N_{54}O_{33}S_3$, and the amino acid sequence of the Spampcin$_{56-86}$ is shown in SEQ ID NO: 01.

A second technical solution is as follows.

A method for preparing the Spampcin$_{56-86}$ comprises synthesizing the Spampcin$_{56-86}$ by a chemical solid-phase method.

A third technical solution is as follows.

An application for using the Spampcin$_{56-86}$ comprises preparing an anti-bacterial agent using the Spampcin$_{56-86}$.

In a preferred embodiment, the anti-bacterial agent has inhibitory or bactericidal effects against *Staphylococcus aureus*, *Staphylococcus epidermidis*, *Enterococcus faecium*, *Enterococcus faecalis*, *Listeria monocytogenes*, *Escherichia coli*, *Pseudomona aeruginosa*, *Aeromonas hydrophila*, *Aeromonas sobria*, *Edwardsiella tarda*, *Pseudomonas fluorescens*, *Acinetobacter baumannii*, drug-resistant *Staphylococcus aureus*, drug-resistant *Acinetobacter baumannii*, and drug-resistant *Escherichia coli*.

A fourth technical solution is as follows.

An application for using the Spampcin$_{56-86}$ comprising preparing an antifungal agent using the Spampcin$_{56-86}$.

In a preferred embodiment, the anti-fungal agent has inhibitory and bactericidal effects against *Fusarium oxysporum*, *Fusarium graminearum*, or *Fusarium solani*.

A fifth technical solution is as follows.

An application for using the Spampcin$_{56-86}$ comprises preparing an aquatic feed additive using the Spampcin$_{56-86}$.

In a preferred embodiment, an active component of the aquatic feed additive comprises the Spampcin$_{56-86}$.

The present disclosure has the following advantages:

The Spampcin$_{56-86}$ of the present disclosure consists of 31 amino acids with a molecular formula of $C_{154}H_{256}N_{54}O_{33}S_3$, and a molecular weight of 3488.25 Daltons. The Spampcin$_{56-86}$ contains 7 positively charged amino acid residues, and the isoelectric point of the Spampcin$_{56-86}$ is 11.71. The average hydrophilicity coefficient of the Spampcin$_{56-86}$ is −0.410, and the Spampcin$_{56-86}$ is a positively charged cationic peptide.

The Spampcin$_{5-86}$ of the present disclosure has a significant anti-bacterial effect on Gram-positive bacteria, Gram-negative bacteria, and fungi. Further, the Spampcin$_{56-86}$ has no obvious cytotoxic effect on hemocytes of *Scylla paramamosain* and human embryonic kidney 293T cells (HEK 293T cells).

The Spampcin$_{56-86}$ of the present disclosure has wide antimicrobial spectrum, strong antibacterial activity, strong antifungal activity, and a rapid bactericidal rate.

The Spampcin$_{56-86}$ can be developed as anti-bacterial drugs and anti-fungal drugs and can also be applied to aquatic feed additives, which has a broad application prospect.

DETAILED DESCRIPTION OF THE EMBODIMENTS

Figure 1A:
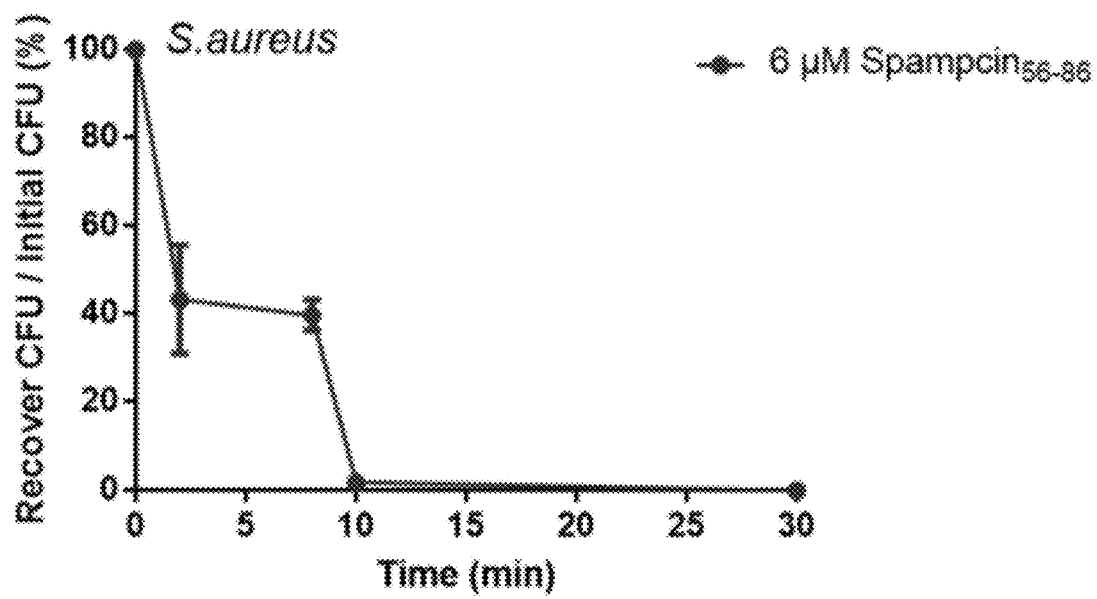
FIGS. 1A, 1B, 1C, and 1D respectively show bactericidal kinetics of the antimicrobial peptide Spampcin$_{56-86}$ of *Scylla paramamosain* (i.e., Spampcin$_{56-86}$) against *Staphylococcus aureus* (i.e., *S. aureus*), *Pseudomonas aeruginosa* (i.e., *P. aeruginosa*), *Aeromonas hydrophila* (i.e., *A. hydrophila*), and *Escherichia coli* (i.e., *E. coli*) in Embodiment 3 of the present disclosure. The X-axes are time (minutes), and the Y-axes are bactericidal rates (%)
Figure 1B:
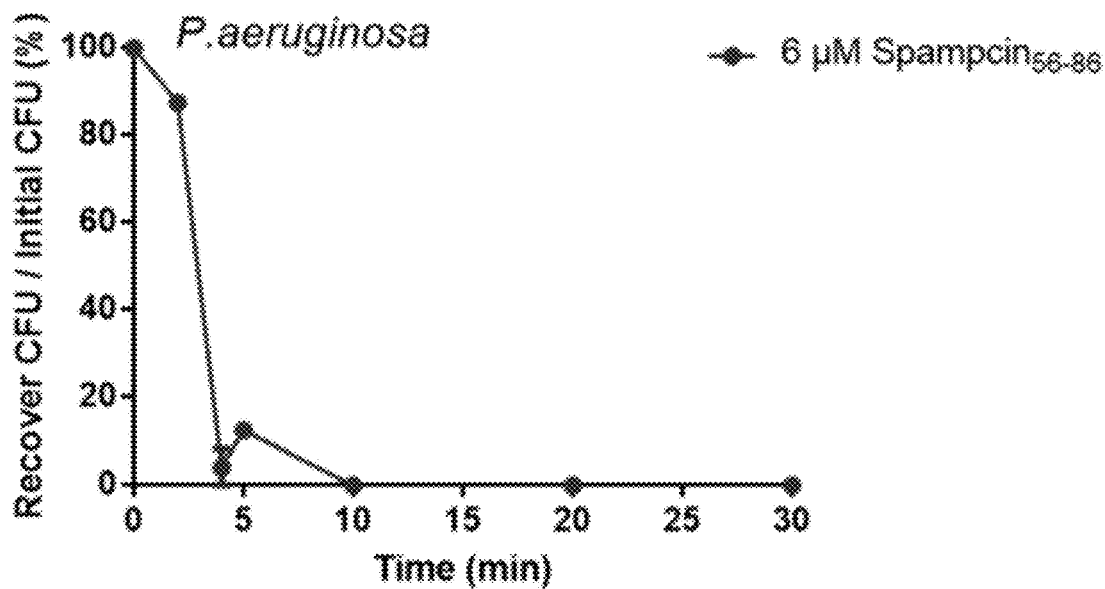
Figure 1C:
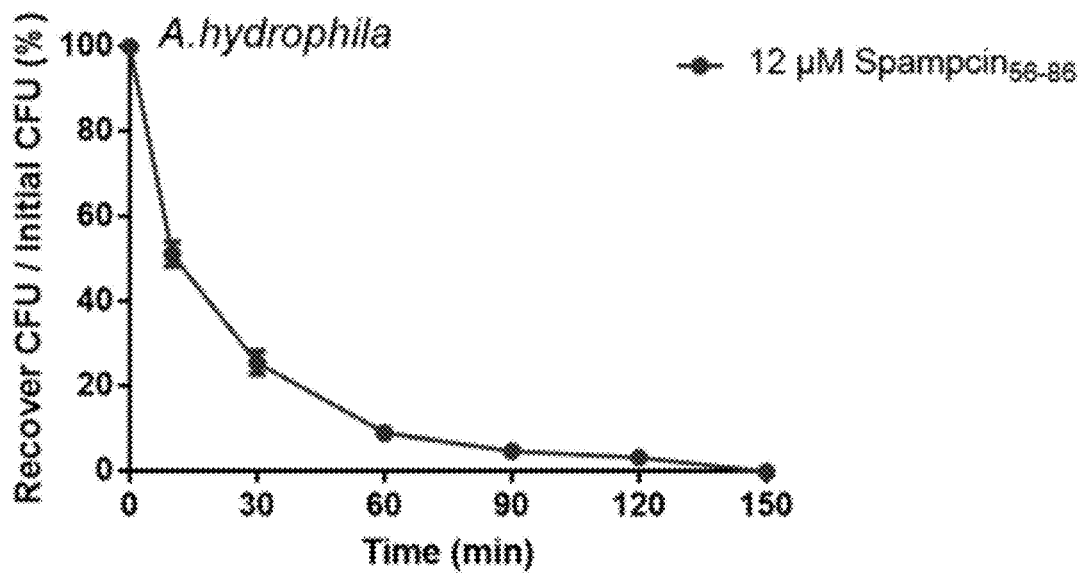
Figure 1D:
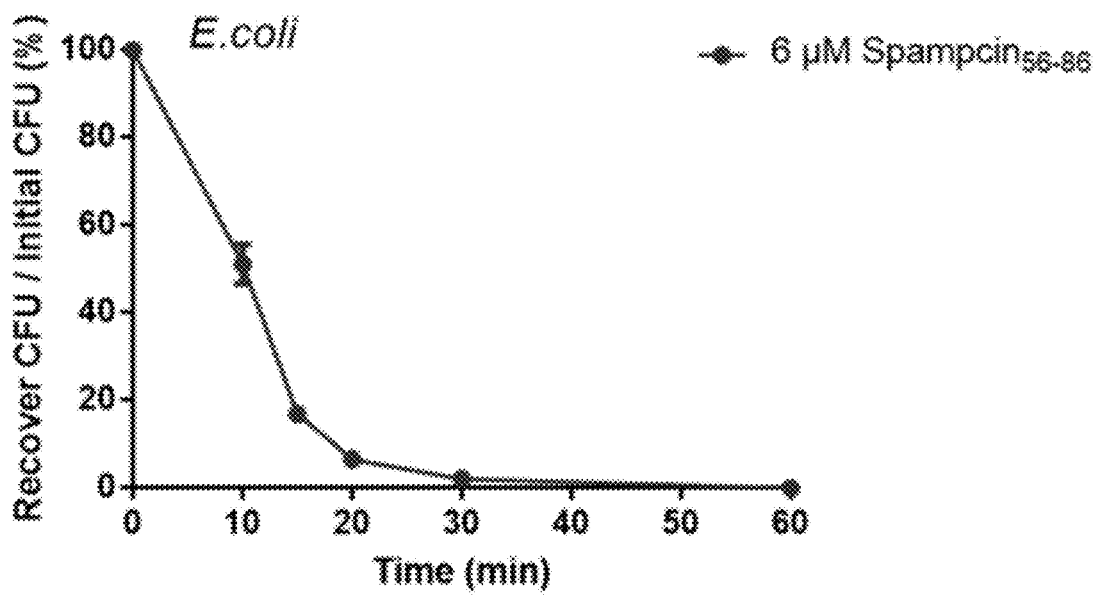

The technical solution of the present disclosure will be further described below in combination with the accompanying embodiments and drawings.

Embodiment 1: Preparation of an Antimicrobial Peptide Spampcin$_{56-86}$ from *Scylla paramamosain* (i.e., Spampcin$_{56-86}$)

An amino acid sequence of Spampcin$_{56-86}$ is as follows: Arg-Arg-Ala-Ala-His-Gly-Leu-Leu-Pro-Arg-Leu-Arg-Ala-Pro-Pro-Pro-Phe-His-Lys-Arg-Cys-Val-Cys-Leu-Cys-Arg-Thr-Ala-Pro-Pro-Pro (SEQ ID NO: 01)

The Spampcin$_{56-86}$ was entrusted to Kingsley (Jiangsu) Co., Ltd. for chemical solid-phase synthesis, and the Spampcin$_{56-86}$ was obtained with a purity of more than 95%. Physicochemical parameters of the Spampcin$_{56-86}$ are shown in Table 1.

TABLE 1

Physicochemical parameters of the Spampcin$_{56-86}$

| Physicochemical parameters | Spampcin$_{56-86}$ |
|---|---|
| Amino acid residue | 31 |
| Molecular weight | 3488.25 |
| Molecular formula | $C_{154}H_{256}N_{54}O_{33}S_3$ |
| Isoelectric point | 11.71 |
| Net charge | +7 |
| Hydrophobicity | 41% |
| Total average hydrophilicity | −0.410 |
| Molar extinction coefficient | 125 |

The Spampcin$_{56-86}$ is a positively charged cationic peptide with a small molecular weight and good stability, as shown in Table 1.

Embodiment 2: Determination of Minimum Inhibitory Concentration (MIC) and Minimum Bactericidal Concentration (MBC) of the Spampcin$_{56-86}$ Bacterial strains involved in Embodiment 2 are as follows: *Staphylococcus aureus* (i.e., *S. aureus*), *Staphylococcus epidermidis* (i.e., *S. epidermidis*), *Enterococcus Faecium* (i.e., *E. Faecium*), *Enterococcus Faecalis* (i.e., *E. Faecalis*), *Listeria Monocytogenes* (i.e., *L. Monocytogenes*), *Escherichia coli* (i.e., *E. coli*), *Pseudomona aeruginosa* (i.e., *P. aeruginosa*), *Aeromonas hydrophila* (i.e., *A. hydrophila*), *Aeromonas sobria* (i.e., *A. sobria*), *Edwardsiella tarda* (i.e., *E. tarda*), *Pseudomonas fluorescens* (i.e., *P. fluorescens*), *Acinetobacter baumannii* (i.e., *A. baumannii*), drug-resistant *S. aureus*, drug-resistant *A. baumannii*, drug-resistant *E. coli*, *Fusarium oxysporum* (i.e., *F. oxysporum*), *Fusarium graminearum* (i.e., *F. graminearum*), or *Fusarium solani* (i.e., *F. solani*). *A. sobria* and *E. tarda* are obtained from Freshwater Fisheries Research Institute of Fujian. The drug-resistant *S. aureus*, the drug-resistant *A. baumannii*, and the drug-resistant *E. coli* are clinical isolates and are provided by the Second Affiliated Hospital of Fujian Medical University, and the rest of the bacterial strains are purchased from the China General Microbiological Culture Collection Center (CGMCC).

The specific method was as follows:

(1) Bacteria, such as *S. aureus, S. epidermidis, E. faecium, E. faecalis, L. monocytogenes, E. coli, P. aeruginosa, A. hydrophila, A. sobria, E. tarda, P. fluorescens, A. baumannii*, drug-resistant *S. aureus*, drug-resistant *A. baumannii*, and drug-resistant *E. coli* were inoculated on nutrient broth plates and cultured at appropriate temperatures for 18-24 hours. Fungi, such as *F. oxysporum, F. graminearum*, and *F. solani* were inoculated on potato dextrose and cultured at 28° C. for 1-7 days.

(2) The bacteria and the fungi were then inoculated on corresponding culture mediums: the bacteria and the fungi were further cultured for 18-24 hours. The bacteria were washed away from the corresponding culture medium with 10 mMol/L (mM) sodium phosphate buffer (pH=7.4) to obtain a suspension of the bacteria. The suspension of the bacteria was diluted with a mixture of Mueller Hinton (MH) medium and the sodium phosphate buffer to a final concentration of $3.3*10^4$ CFU/mL. Spores of the fungi were washed away from the corresponding culture medium with 10 mM of a sodium phosphate buffer (pH=7.4), and were then diluted with a mixture of the potato dextrose liquid and the sodium phosphate buffer. The concentration of the spores was determined under an optical microscope and adjusted to a final concentration of $5*10^4$ cells/mL.

(3) The Spampcin$_{56-86}$ was dissolved in sterilized MilliQ® water, filtered by a 0.22 μm pore size membrane, diluted to concentrations of 3 μM, 6 μM, 12 μM, 12 μM, 24 μM, 48 μM, and 96 μM, and placed on ice for use.

(4) A blank control group, a negative control group, and an experimental group of each of the bacteria and the fungi were set on 96-well cell culture plates, and each of the blank control group, the negative control group, and the experimental group has three parallel samples.

The blank control group a: 50 μL of the Spampcin$_{56-86}$ with 50 μL of the corresponding culture medium;

The negative control group b: 50 μL of sterilized MilliQ® water with 50 μL of the suspension of the bacteria or the suspension of the fungi; and The experimental group c: 50 μL of the Spampcin$_{56-86}$ with 50 μL of the suspension of the bacteria or the suspension of the fungi.

(5) The 96-well cell culture plates were placed in an incubator at 28° C. and cultured for 1-2 days.

The results of MIC and MBC of the Spampcin$_{56-86}$ are shown in Table 2.

TABLE 2

Anti-bacterial activity and anti-fungal activity of the Spampcin$_{56-86}$

| Microorganism | CGMC NO. | MIC | MBC |
|---|---|---|---|
| Gram-positive bacterium | | | |
| S. aureus | 1.2465 | 1.5-3 | 3-6 |
| L. monocytogenes | 1.10753 | 1.5-3 | 1.5-3 |
| E. faecalis | 1.2135 | 1.5-3 | 1.5-3 |
| E. faecium | 1.131 | 0-1.5 | 1.5-3 |
| S. epidermidis | 1.4260 | 3-6 | 3-6 |
| S. aureus QZ19133 | — | 6-12 | 6-12 |
| S. aureus QZ19132 | — | 6-12 | 12-24 |
| Gram-negative bacterium | | | |
| P. aeruginosa | 1.2421 | 1.5-3 | 3-6 |
| A. baumannii | 1.6769 | 3-6 | 3-6 |
| A. sobria | — | 3-6 | 3-6 |
| A. hydrophila | 1.2017 | 6-12 | 6-12 |
| E. coli | 1.2389 | 3-6 | 3-6 |
| E. tarda | — | 3-6 | 24-48 |
| P. fluorescens | 1.3202 | 1.5-3 | 1.5-3 |
| E. coli QZ20147 | — | 6-12 | 6-12 |
| E. coli QZ20148 | — | 6-12 | 6-12 |
| A. baumannii QZ20142 | — | 3-6 | 3-6 |
| A. baumannii QZ20143 | — | 3-6 | 6-12 |
| Fungi | | | |
| F. oxysporum | 3.6785 | 3-6 | 3-6 |
| F. graminearum | 3.4521 | 1.5-3 | 1.5-3 |
| F. solani | 3.5840 | 1.5-3 | 3-6 |

Note:
a-b represent minimum inhibitory concentration (MIC) (μM) and minimum bactericidal concentration (MBC) (μM).
a: The highest concentration of the Spampcin$_{56-86}$ that induce visible growth of microorganisms.
b: The lowest concentration of the Spampcin$_{56-86}$ that does not induce visible growth of microorganisms.

Embodiment 3: A bactericidal Kinetic Curve of the Spampcin$_{56-86}$

Staphylococcus Aureus (i.e., S. aureus), Pseudomona Aeruginosa (i.e., P. aeruginosa), Aeromonas hydrophila (i.e., A. hydrophila), and Escherichia coli (i.e., E. coli) were selected to test bactericidal kinetics of the Spampcin$_{56-86}$.

A specific method in Embodiment 3 is similar to the antimicrobial activity assay described in Embodiment 2. A final concentration of the Spampcin$_{56-86}$ was adjusted to 1×MBC (S. aureus: 6 μMol/L (μM); P. aeruginosa: 6 μM; A. hydrophila: 12 μM; and E. coli: 6 μM).

At 2, 8, 10, 20, 25, and 30 minutes of incubation, 6 μL of a suspension of S. aureus was diluted into 600 μL of Dulbecco's phosphate-buffered saline (DPBS) to obtain a first solution, 20 μL of the first solution was coated on a nutrient broth plate, and cultured at 37° C. for 1-2 days to record the number of S. aureus monoclonal, and the percentage of Colony-Forming Units (CFU) was calculated.

At 2, 4, 5, 10, 15, 20, and 30 minutes of incubation, 6 μL of the suspension of P. aeruginosa was diluted using 600 μL of the DPBS to obtain a second solution, 40 μL of the second solution was coated on the nutrient broth plate, and cultured at 37° C. for 1-2 days to record the number of P. aeruginosa monoclonal, and the percentage of CFU was calculated.

At 10, 30, 60, 120, and 150 minutes of incubation, 6 μL of the suspension of A. hydrophila was diluted using 720 μL of the DPBS to obtain a third solution, and 20 μL of the third solution was coated on the nutrient broth plate, and cultured at 28° C. for 1-2 days to record the number of A. Hydrophila monoclonal, and the percentage of CFU was calculated.

At 10, 15, 20, 30, and 60 minutes of incubation, 6 μL of the suspension of E. coli l was diluted using 720 μL of the DPBS to obtain a fourth solution, and 20 μL of the fourth solution was coated on the nutrient broth plate, and cultured at 37° C. for 1-2 days to record the number of E. coli monoclonal, and the percentage of CFU was calculated.

Referring to FIGS. 1A, 1B, 1C, and 1D, the percentage of CFU is defined relative to the CFU obtained in the control group.

Embodiment 4: The Thermal Stability of Anti-Bacterial Activity of the Spampcin$_{56-86}$ Staphylococcus aureus (i.e., S. aureus) and Pseudomona aeruginosa (i.e., P. aeruginosa) were selected to test the thermal stability of the anti-bacterial activity of the Spampcin$_{56-86}$.

Figure 2A:
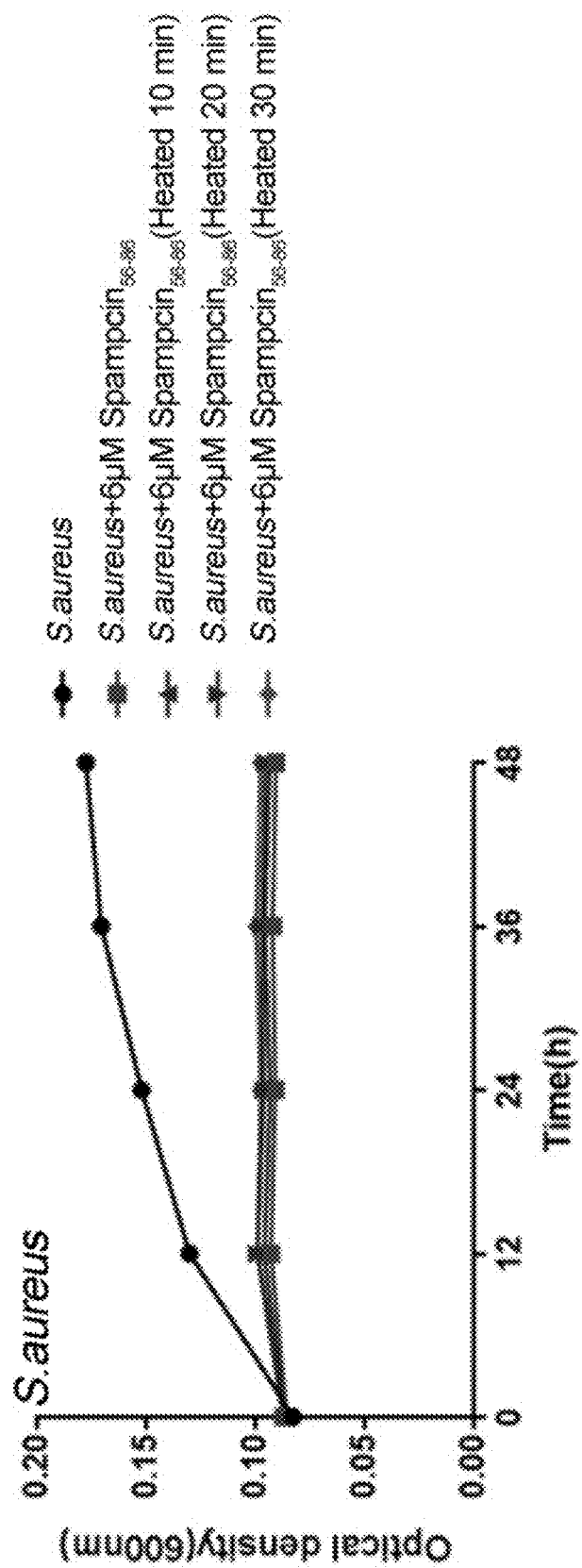
FIGS. 2A and 2B respectively show the thermal stability of Spampcin$_{56-86}$ against *S. aureus* and *P. aeruginosa* in Embodiment 4 of the present disclosure. The X-axes are time (hours), and the Y-axes are the OD$_{600}$ values.
Figure 2B:
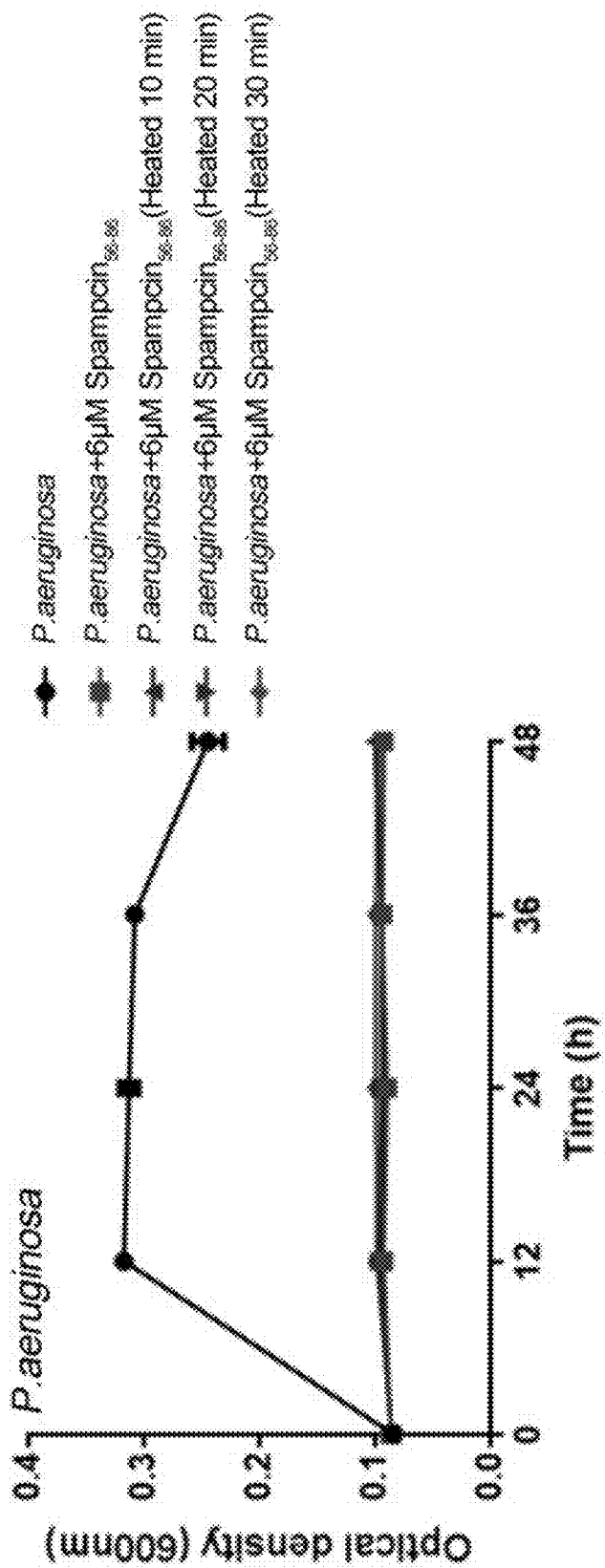
Figure 3A:
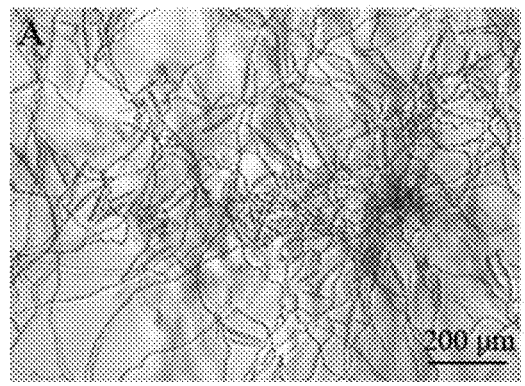
FIGS. 3A, 3B, and 3C show the inhibition of Spampcin$_{56-86}$ against *Fusarium graminearum* (i.e., *F. graminearum*) spore germination in Embodiment 5 of the present disclosure. The concentrations of Spampcin$_{56-86}$ are 0 μMol (μM), 6 μM, and 12 μM, respectively.
Figure 3B:
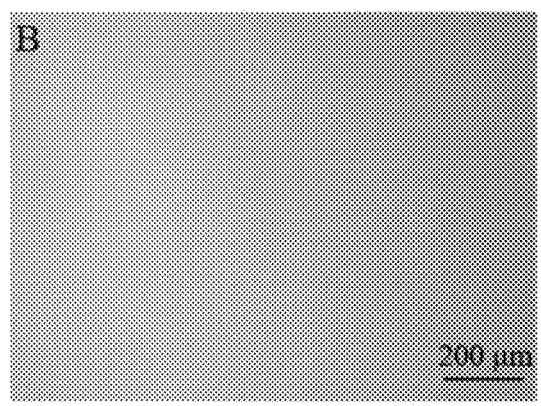
Figure 3C:
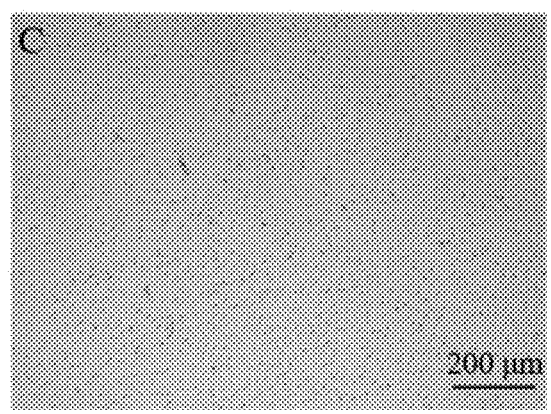
Figure 4A:
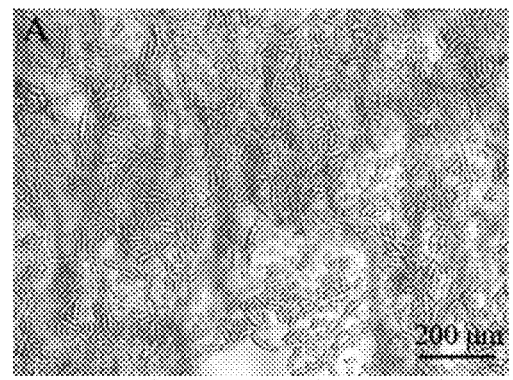
FIGS. 4A, 4B, and 4C show the inhibition of Spampcin$_{56-86}$ against *Fusarium oxysporum* (i.e., *F. oxysporum*) spore germination in Embodiment 5 of the present disclosure. The concentrations of Spampcin$_{56-86}$ are 0 μM, 6 μM, and 12 μM, respectively.
Figure 4B:
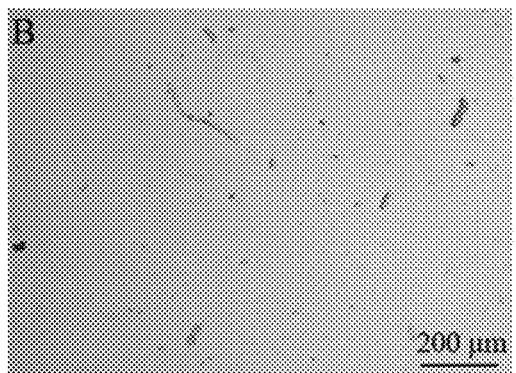
Figure 4C:
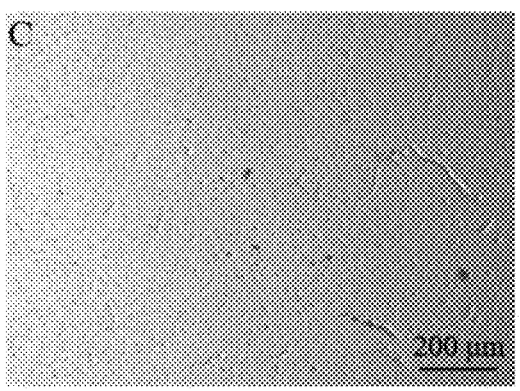
Figure 5A:
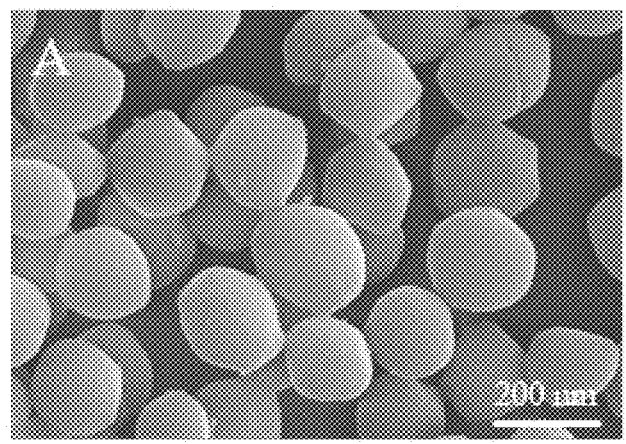
FIG. 5A shows morphological changes of *S. aureus* without treatment, and FIG. shows morphological changes of *S. aureus* after treatment with 12 μM Spampcin$_{56-86}$ in Embodiment 6 of the present disclosure under scanning electron microscope (SEM) observation.
Figure 5B:
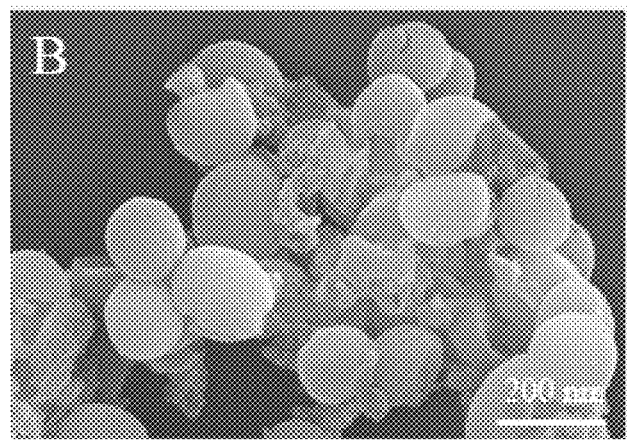
Figure 6A:
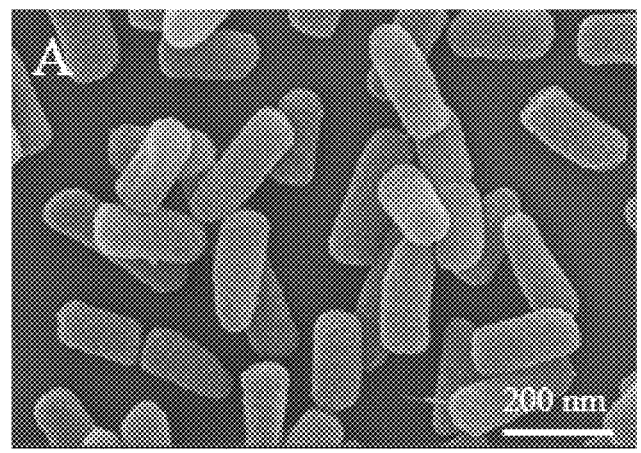
FIG. 6A shows morphological changes of *P. aeruginosa* without treatment.
Figure 6B:
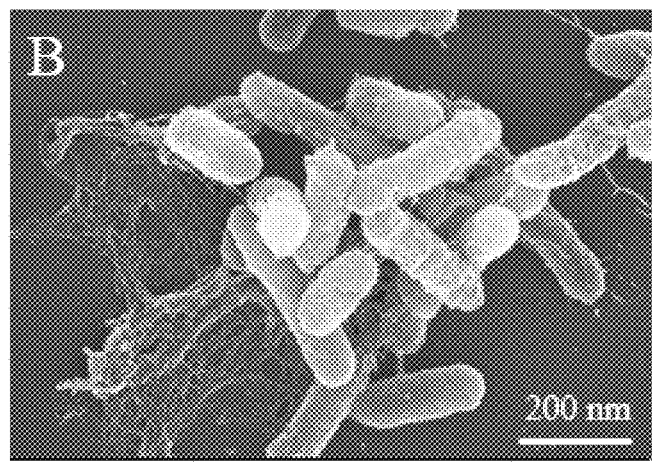
FIG. 6B illustrates morphological changes of *P. aeruginosa* after treatment with 12 μM of Spampcin$_{56-86}$ under SEM observation in Embodiment 6 of the present disclosure.

A specific method in Embodiment 4 is similar to the antimicrobial activity assay described in Embodiment 2. A final concentration of the Spampcin$_{56-86}$ was adjusted to 1×MBC (S. aureus: 6 μMol/L (μM), P. aeruginosa: 6 μM) to obtain a Spampcin$_{56-86}$ solution. The Spampcin$_{56-86}$ solution was heated in boiling water for 10, 20, and 30 minutes, and then placed on ice for use. The Spampcin$_{56-86}$ was co-cultured with S. aureus or P. aeruginosa. $OD_{600}$ values were measured with a microplate reader at 0, 12, 24, 36, and 48 hours, and the results are shown in FIGS. 2A and 2B.

Embodiment 5: Microscopic Observations of Spore Germination of Fungi after Treatment with the Spampcin$_{56-86}$ Fusarium oxysporum (i.e., F. oxysporum) and Fusarium graminearum (i.e., F. graminearum) were selected to evaluate the effects of the Spampcin$_{56-86}$ on the spore germination of the fungi.

A specific method in Embodiment 5 is similar to the antimicrobial activity assay described in Embodiment 2. The concentration of the Spampcin$_{56-86}$ was adjusted to be 6 μMol/L (μM) and 12 μM. A final concentration of spores of F. oxysporum and F. graminearum was adjusted to be $5*10^4$ cells/mL. Each of the Spampcin$_{56-86}$ with the concentration of 6 μM and 12 μM and a corresponding one of the spores of *F. oxysporum* and *F. graminearum* were mixed to even in 96-well cell culture plates, and cultured for 24 hours at 28° C. The spore germination of *F. oxysporum* and *F. graminearum* was observed under an optical microscope, as shown in FIGS. 3A, 3B, 3C, 4A, 4B, and 4C.

Embodiment 6: Scanning Electron Microscope (SEM) Observation of Bacteria after Treatment with the Spampcin$_{56-86}$

*Staphylococcus aureus* (i.e., *S. aureus*) and *Pseudomona aeruginosa* (i.e., *P. aeruginosa*) were selected as testing strains, and a method for preparing SEM samples comprises the following steps:

(1) A suspension of *S. aureus* and *P. aeruginosa* (OD$_{600}$=0.4) are prepared according to the method described in Embodiment 2.

(2) The Spampcin$_{56-86}$ was dissolved with sterilized pure water and placed on ice for use, and the concentration of the Spampcin$_{56-86}$ was adjusted to be 12 μMol/L (μM) Spampcin$_{56-86}$.

(3) The suspension of *S. aureus* was treated with the 12 μM Spampcin$_{56-86}$ with the same volume as the suspension of *S. aureus* at 37° C. for 10 minutes, and the suspension of *P. aeruginosa* was treated with the 12 μM Spampcin$_{56-86}$ with the same volume as the suspension of *P. aeruginosa* at 37° C. for 30 minutes.

(4) A fixative solution of glutaraldehyde with the same volume as the 12 μM Spampcin$_{56-86}$ was added, fixed at 4° C. for 2 hours to obtain first samples.

(5) The first samples were dehydrated in a series of concentration of 30%, 50%, 70%, 80%, 90%, 95%, 100%, and 100% (volume/volume (v/v)) of ethanol for 15 minutes to obtain second samples.

(6) After a gold spray, the second samples are observed and photographed by a scanning electron microscope (SEM). The results are shown in FIGS. 5A, 5B, 6A, and 6B.

Embodiment 7: Determination of Cytotoxicity of the Spampcin$_{56-86}$

Human embryonic kidney 293T cells (HEK-293T) and hemocytes of *Scylla paramamosain* (i.e., *S. paramamosain*) were selected to test the cytotoxicity effects of the Spampcin$_{56-86}$.

(1) The hemocytes of *S. paramamosain* and HEK-293T were harvested, and the cell concentrations of the hemocytes of the *S. paramamosain* and HEK-293T are adjusted to 1×10$^5$ cells/mL to obtain cell suspensions. 100 μL of the cell suspensions were seeded in 96-well cell culture plates, and incubated at an appropriate temperature.

(2) The hemocytes of the *S. paramamosain* and HEK-293T were treated with the Spampcin$_{56-86}$ with different concentrations of (0, 3, 6, 12, 24, and 48 μM) for 24 hours.

Figure 7A:
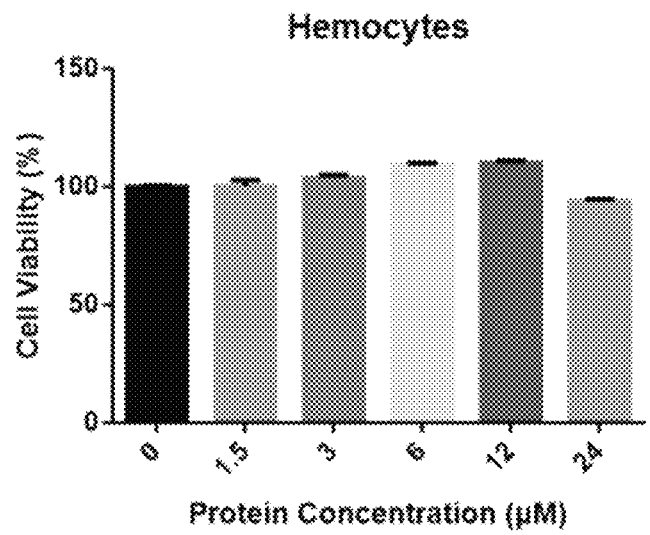
FIGS. 7A and 7B illustrate graphs of a cytotoxicity test of Spampcin$_{56-86}$ using a 3-(4,5-dimethylthiazol-2-yl)-5-(3-carboxymethoxyphenyl)-2-(4-sulfophenyl)-2H-tetrazolium-phenazine methosulfate (MTS-PMS) assay. The X-axes are concentrations (μM) of Spampcin$_{56-86}$, and the Y-axes are cell proliferation rates (%).
Figure 7B:
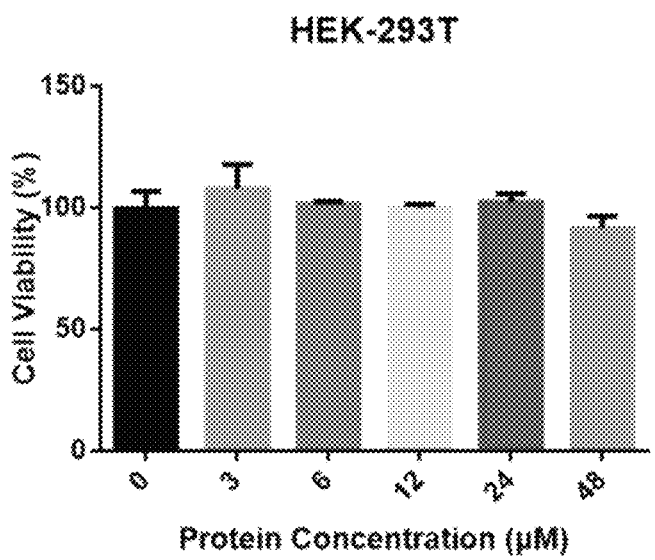

(3) The hemocytes of the *S. paramamosain* and HEK-293T were treated with 20 μL of a 3-(4,5-dimethylthiazol-2-yl)-5-(3-carboxymethoxyphenyl)-2-(4-sulfophenyl)-2H-tetrazolium-phenazine methosulfate (MTS-PMS) reagent for another 2 hours, and then an absorbance value of each well of the 96-well cell culture plates was measured at 492 nm using a microplate reader to evaluate the cytotoxicity of the Spampcin$_{56-86}$, and the results are shown in FIGS. 7A and 7B.

The aforementioned embodiments are merely some embodiments of the present disclosure, and the scope of the disclosure is not limited thereto. Thus, it is intended that the present disclosure cover any modifications and variations provided they are made without departing from the appended claims and the specification of the present disclosure.

What is claimed is:

1. An antimicrobial peptide Spampcin$_{56-86}$ from *Scylla paramamosain*, wherein:
   the molecular formula of the antimicrobial peptide Spampcin$_{56-86}$ is $C_{154}H_{256}N_{54}O_{33}S_3$, and
   the amino acid sequence of the antimicrobial peptide Spampcin$_{56-86}$ is shown in SEQ ID NO: 01.

2. A method for using the antimicrobial peptide Spampcin$_{56-86}$ according to claim 1, comprising:
   preparing an antimicrobial agent using the antimicrobial peptide Spampcin$_{56-86}$, wherein:
      the antimicrobial agents has inhibitory or bactericidal effects on *Staphylococcus aureus*, *Staphylococcus epidermidis*, *Enterococcus faecium*, *Enterococcus faecalis*, *Listeria monocytogenes*, *Escherichia coli*, *Pseudomona aeruginosa*, *Aeromonas hydrophila*, *Aeromonas sobria*, *Edwardsiella tarda*, *Pseudomonas fluorescens*, *Acinetobacter baumannii*, drug-resistant *Staphylococcus aureus*, drug-resistant *Acinetobacter baumannii*, and drug-resistant *Escherichia coli*.

3. A method for using the antimicrobial peptide Spampcin$_{56-86}$ according to claim 1, comprising:
   preparing an anti-fungal agent using the antimicrobial peptide Spampcin$_{56-86}$, wherein:
      the anti-fungal agent has inhibitory or bactericidal effects on *Fusarium oxysporum*, *Fusarium graminearum*, or *Fusarium solani*.

4. A method for using the antimicrobial peptide Spampcin$_{56-86}$ according to claim 1, comprising:
   preparing an aquatic feed additive using the antimicrobial peptide Spampcin$_{56-86}$ in preparation.

5. An application method for using the antimicrobial peptide Spampcin$_{56-86}$ according to claim 1, comprising:
   inhibiting or killing *Staphylococcus aureus*, *Staphylococcus epidermidis*, *Enterococcus faecium*, *Enterococcus faecalis*, *Listeria monocytogenes*, *Escherichia coli*,

*Pseudomona aeruginosa, Aeromonas hydrophila, Aeromonas sobria, Edwardsiella tarda, Pseudomonas fluorescens, Acinetobacter baumannii*, drug-resistant *Staphylococcus aureus*, drug-resistant *Acinetobacter baumannii*, and drug-resistant *Escherichia coli* using the antimicrobial peptide Spampcin$_{56-86}$.

6. A method for using the antimicrobial peptide Spampcin$_{56-86}$ according to claim 1, comprising:
inhibiting or killing *Fusarium oxysporum, Fusarium graminearum*, or *Fusarium solani* using the antimicrobial peptide Spampcin$_{56-86}$.

\* \* \* \* \*